United States Patent

Musser et al.

[11] Patent Number: 4,547,509
[45] Date of Patent: Oct. 15, 1985

[54] 5,6,7-QUINOLINE CARBANILATES AND METHOD OF TREATING ISCHEMIC HEART DISEASE THEREWITH

[75] Inventors: John H. Musser, Malvern, Pa.; Charles A. Sutherland, Hawthorne, N.Y.

[73] Assignee: USV Pharmaceutical Corp., Tarrytown, N.Y.

[21] Appl. No.: 455,392

[22] Filed: Jan. 3, 1983

[51] Int. Cl.[4] .................... C07D 215/20; A61K 31/47
[52] U.S. Cl. .................... 514/311; 546/177; 546/176; 546/171
[58] Field of Search .................... 546/177; 424/258

[56] References Cited

U.S. PATENT DOCUMENTS 3,351,525  11/1967  Hodel .................... 546/168
3,818,012  6/1974   Nikles .................... 546/177
3,946,016  3/1976   Karsten .................. 424/258 X

FOREIGN PATENT DOCUMENTS 1484002  6/1967   France .
1510067  11/1967  France .
67/6898  11/1967  South Africa .

OTHER PUBLICATIONS

Chem. Abst. 67: 21843a, (1967) of Meth. Appl. 6,606,695, (1966).

Primary Examiner—Glennon H. Hollrah
Assistant Examiner—D. Springer

[57] ABSTRACT

Compounds of the structure

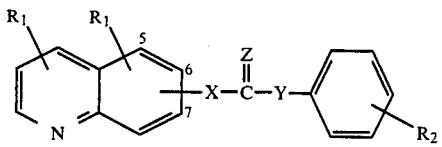

and pharmaceutically acceptable salts thereof wherein:
$R_1$ is H, alkyl, alkoxy, carboxyl, alkylcarboxy, acylamino, dialkyl amino, trihalomethyl, halogen, nitro, hydroxy or cyano;
X is in the 5, 6 or 7 position and is $O(CH_2)_n$, $N(CH_2)_n$—$R_3$, $S(CH_2)_n$ or $(CH_2)_n$;
Y is $O(CH_2)_n$, $S(CH_2)_n$, $N(CH_2)_n$—$R_3$ where $R_3$ is H, alkyl or $(CH_2)_n$;
$R_2$ is monosubstituted or independently disubstituted H, hydroxy, alkyl, halogen, nitro, alkoxy, carboxyl, alkylcarboxy, trihalomethyl, cyano, trifluoromethyl, dialkylamino or acylamino;
Z is O, S or $(NR_3)_2$ where $R_3$ is H, alkyl or aryl; and
n is 0 to 10 inclusive useful in the treatment of ischemic heart disease and hypertriglyceridemia.

15 Claims, No Drawings

5,6,7-QUINOLINE CARBANILATES AND METHOD OF TREATING ISCHEMIC HEART DISEASE THEREWITH

DESCRIPTION OF THE PRIOR ART

We have found that quinoline carbanilates are active antilipolytic agents as evidenced by the myocardial lipase and the rat adipocyte asays.

Lipolysis is associated with ischemic heart disease: free fatty acid has a detrimental effect on the ischemic heart by disrupting electrical conduction, decreasing myocardial efficiency and preventing the transfer of adenosine diphosphate and adenosine triphosphate, in and out, respectively, of the mitochondria. Interventions which depress myocardial oxygen consumption in animals and man provide a protective effect against ischemic injury.

The object of this invention is to provide compounds capable of inhibiting lipolysis associated with ischemic heart disease.

We have found that 5-, 6-, 7-, and 8- quinoline carbanilates are active antilipolytic agents. While 5-, 6- and 7- quinoline carbanilates are new chemical compounds, 8-quinoline carbanilates are known as fungicides, pesticides, amebicides and bactericides.

DESCRIPTION OF THE INVENTION

This invention relates to new chemical compounds possessing valuable pharmaceutical activity. It relates particularly to compounds useful in the treatment of ischemic heart disease and hypertriglyceridemia and having the structure:

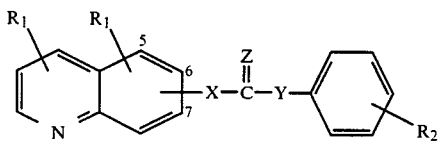

and pharmaceutically acceptable salts thereof wherein:
- $R_1$ is H, alkyl, alkoxy, carboxyl, alkylcarboxy, acylamino, dialkylamino, trihalomethyl, halogen nitro, hydroxy or cyano;
- X is in the 5, 6 or 7 position and is $O(CH_2)_n$, $N(CH_2)_n-R_3$, $S(CH_2)_n$ or $(CH_2)_n$;
- Y is $O(CH_2)_n$, $S(CH_2)_n$, $N(CH_2)_n-R_3$ where $R_3$ is H, alkyl or $(CH_2)_n$;
- $R_2$ is monosubstituted or independently disubstituted H, hydroxy, alkyl, halogen, nitro, alkoxy, carboxyl, alkylcarboxy, trihalomethyl, cyano, dialkylamino or acylamino;
- Z is O, S or $(NR_3)_2$ where $R_3$ is H, alkyl or aryl; and
- n is 0 to 10 inclusive useful in the treatment of ischemic heart disease and hypertriglyceridemia.

The alkyl group and the alkyl moieties in alkoxy and alkylcarboxy contain 1 to 7 carbon atoms and may be a straight or a branched chain. Such groups include methyl, ethyl, propyl, isopropyl, butyl, isobutyl, amyl, isoamyl and the like.

The trihalo and halogen is F, Cl, Br or I.

The aryl group is preferably phenyl or naphthyl.

The compounds of this invention may be readily prepared by reacting the appropriate quinolinol with various substituted phenyl isocyanates. The reaction is thermally reversible and for that reason the preferred procedure involves the mixing of the two reactants in ethyl ether with a small amount of triethylamine present as a catalyst and stirring at room temperature for several days.

The schematic procedure is as follows:

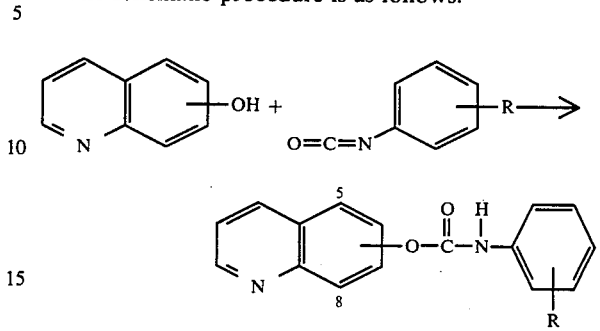

The desired starting materials and intermediates can be prepared from readily available materials using standard organic reactions. Some starting materials and intermediates are also available from chemical supply companies, such as Aldrich and Pfaltz & Bauer.

The invention will be more fully illustrated in the examples that follow. These examples are given by way of illustration and are not to be considered as limiting.

EXAMPLE 1

To a solution of 7-hydroxyquinoline (1.45 g., Pfaltz & Bauer HI17880) and 4-methoxyphenyl isocyanate (1.49 g.) in ethyl ether (100 ml) was added triethylamine (1.4 ml). The reaction was stirred for two days at room temperature. The resulting precipitate was filtered and recrystallized from ethyl ether.

In like manner as above, using appropriate starting materials and reagents, the following compounds were prepared:

EXAMPLE 2
6-quinolyl-4-methoxy carbanilate

EXAMPLE 3
5-quinolyl-4-methoxy carbanilate

EXAMPLE 4
7-quinolyl-2-methoxy carbanilate

EXAMPLE 5
6-quinolyl-2-methoxy carbanilate

EXAMPLE 6
5-quinolyl-2-methoxy carbanilate

EXAMPLE 7
7-quinolyl-3-methoxy carbanilate

EXAMPLE 8
7-quinolyl-4-carbethoxy carbanilate

EXAMPLE 9
7-quinolyl-2-chloro carbanilate

EXAMPLE 10
7-quinolyl-2-methyl carbanilate

EXMPLE 11
7-quinolyl-2-trifluoromethyl carbanilate

EXAMPLE 12

7-quinolyl-4-methoxy phenethyl carbamate

The compounds of the present invention exhibed activity in the myocardial lipase assay and the rat adipocyte assay.

Myocardial Lipase Assay

All compounds were dissolved in DMSO (final concentration 3.0%) and tested in duplicate at a concentration of 100 μm. Canine cardiac lipases were obtained by extracting washed heart membranes with buffer plus heparin and a small amount of Triton X-100 detergent. Because these enzymes are only active at an oil-water interface, the enzyme reaction is run in an oil-water emulsion that contains triolein substrate, Tris buffer (50 mM, pH 6.8) and a small amount of bovine serum albumin (0.5%) added to stabilize the emulsion. A small amount of tritiated triolein was added to the unlabelled triolein substrate. Tritium-labelled oleic acid released by the lipases was extracted into hexane, separated from unreacted triolein and counted in a scintillation counter. Inhibitory agents reduce the amount of radioactivity appearing in the free fatty acid fraction isolated in the extraction procedure.

Rat Adipocyte Assay

Abdominal fat pads were removed from male rats weighing 200-250 grams and placed in Krebs-bicarbonate buffer gassed with 95% $O_2$/5% $CO_2$. The fat pads were digested with collagenase for 1 hour at 37° C., washed twice with Krebs-bicarbonate buffer and distributed among a set of 20 ml plastic counting vials. Two such vials received only buffer and cells (4 ml) but no angonists or antagonists. The remaining vials received epinephrine (3 μM) plus the phosphodiesterase inhibitor methylisobutylxanthine (10 μM). Test compounds were dissolved in DMSO or water to a concentration of 20 mM or 40 μl was added to the buffer plus cells in the counting vials. The final compound concentration for routine screening was 200 μM (final concentration of DMSO=1%).

The cells were incubated for 1 hour at 37° C. under 95% $O_2$/5% $CO_2$ atmosphere. The incubation was stopped by placing the vials in crushed ice. The cells and medium were transferred to test tubes, centrifuged and the cell layer removed by aspiration. The aqueous phase was assayed for glycerol using the enzyme glycerol dehydrogenase.

The glycerol dehydrogenase assay for glycerol depends on the enzyme catalyzed conversion of glycerol to glyceraldehyde and NAD to NADH. The assay can detect as little as 5-10 nanomoles of glycerol. The aqueous phase, following removal of cells, usually contained about 50 to 80 nanomoles of glycerol per 300 μl of assayed sample if no inhibitory activity was present. Samples from the control tubes (no agonist) usually contained 0-5 nanomoles of glycerol per 300 μl of sample.

The results obtained on representative compounds of the present invention are shown in Table I.

The therapeutic compounds of this invention may be administered to a mammal alone or in combination with pharmaceutically acceptable carriers, the proportion of which is determined by the solubility and chemical nature of the compound, chosen route of administration and standard pharmaceutical practice.

The physician will determine the dosage of the present therapeutic agents which will be most suitable and it will vary with the form of administration and the particular compound chosen, and also, it will vary with the particular patient under treatment. He will generally wish to initiate treatment with small dosages substantially less than the optimum dose of the compound and increase the dosage by small increments until the optimum effect under the circumstances is reached. The therapeutic dosage will generally be from a couple of mg. to about 30 mg/kg of body weight or higher.

TABLE I
INHIBITION OF MYOCARDIAL LIPASE AND RAT ADIPOCYTE LIPOLYSIS BY QUINOLINE CARBANILATES

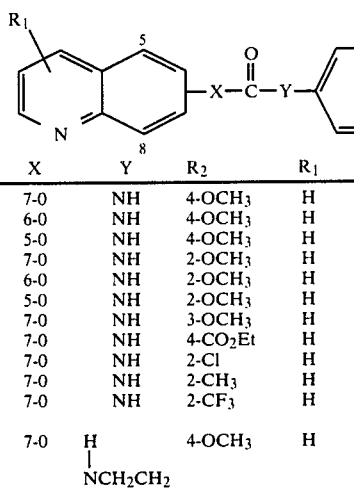

| No. | X | Y | $R_2$ | $R_1$ | M.P. (°C.) | Lipase $I_{50}$ μM or % Inh. at 100 μM | Adipocyte $I_{50}$ μM or % Inhib. at μM |
|---|---|---|---|---|---|---|---|
| 1 | 7-O | NH | 4-OCH$_3$ | H | 153-159 | 60% | 0% at 30 μM |
| 2 | 6-O | NH | 4-OCH$_3$ | H | 139-141 | 64% | 8% at 30 μM |
| 3 | 5-O | NH | 4-OCH$_3$ | H | 174-177 | 63% | 1% at 30 μM |
| 4 | 7-O | NH | 2-OCH$_3$ | H | 115-117 | 48 μM | 80 μM |
| 5 | 6-O | NH | 2-OCH$_3$ | H | 112-113 | 42 μM | 30 μM |
| 6 | 5-O | NH | 2-OCH$_3$ | H | 117-118 | 48 μM | 31% at 200 μM |
| 7 | 7-O | NH | 3-OCH$_3$ | H | 136-137 | 52% | 25% at 200 μM |
| 8 | 7-O | NH | 4-CO$_2$Et | H | 180-182 | 46% | 18% at 200 μM |
| 9 | 7-O | NH | 2-Cl | H | 152-154 | 6% | — |
| 10 | 7-O | NH | 2-CH$_3$ | H | 145-147 | 45% | 20% at 200 μM |
| 11 | 7-O | NH | 2-CF$_3$ | H | 235-238 | 12% | — |
| 12 | 7-O | H\|NCH$_2$CH$_2$ | 4-OCH$_3$ | H | 112-115 | 97% | 84% at 100 μM |

What is claimed is:

1. A compound of the structure:

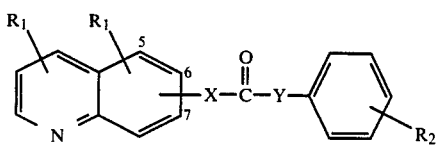

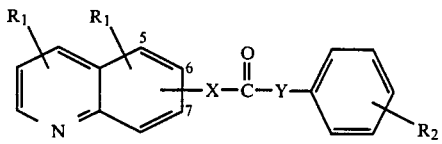

and pharmaceutically acceptable salts thereof wherein:
 R₁ is H, alkyl, alkoxy, carboxyl, alkylcarboxy, lower alkyl carbonyl amido, dialkyl amino, trichloromethyl, tribromomethyl, trifluoromethyl, halogen, nitro, hydroxy or cyano:
 X is in the 5, 6 or 7 position and is O
 Y is N-R₃ where R₃ is H or alkyl;
 R₂ is H, monosubstituted or disubstituted hydroxy, alkyl, halogen, nitro, alkoxy, carboxyl, alkylcarboxy, trichloromethyl, tribromomethyl, trifluoromethyl, cyano, dialkylamino or lower alkyl carbonyl amido;
wherein said alkyl group and the alkyl moieties in alkoxy and alkylcarboxy contain from 1 to 7 carbon atoms.

2. The compound of claim 1 wherein said alkyl group and the alkyl moieties in alkoxy are straight chains.

3. The compound of claim 1 wherein said alkyl group and the alkyl moieties in alkoxy and alkylcarboxy are branched chains.

4. The compound of claim 1 wherein said alkyl group and the alkyl moieties in alkoxy and alkylcarboxy are selected from the group consisting of methyl, ethyl, normal- propyl, isopropyl, normal-butyl, isobutyl, secondary- and tertiary-butyl, normal-amyl, isoamyl, secondary- and tertiary-amyl.

5. A therapeutic composition for inhibiting lipolysis in a mammal which comprises, in combination with at least one pharmaceutically-acceptable extender, an effective amount for the inhibition of lipolysis of a compound of the formula:

and pharmaceutically acceptable salts thereof wherein:
 R₁ is H, alkyl, alkoxy, carboxyl, alkylcarboxy, lower alkyl carbonyl amido, dialkyl amino, trichloromethyl, tribromomethyl, trifluoromethyl, halogen, nitro, hydroxy or cyano;
 X is in the 5, 6 or 7 position and is O,
 Y is N—R₃ where R₃ is H or alkyl;
 R₂ is monosubstituted or disubstituted H, hydroxy, alkyl, halogen, nitro, alkoxy, carboxyl, alkylcarboxy, trichloromethyl, tribromomethyl, trifluoromethyl, cyano, dialkylamino or lower alkyl carbonyl amido;
wherein said alkyl groups and the alkyl moieties in alkoxy and alkylcarboxy contain from 1 to 7 carbon atoms.

6. The therapeutic composition of claim 5 wherein said alkyl group and the alkyl moieties in alkoxy and alkylcarboxy are straight chains.

7. The therapeutic composition of claim 5 wherein said alkyl group and the alkyl moieties in alkoxy and alkylcarboxy are branched chains.

8. The therapeutic composition of claim 5 wherein said alkyl group and the alkyl moieties in alkoxy and alkylcarboxy are selected from the group consisting of methyl, ethyl, normal-propyl, isopropyl, normal-butyl, isobutyl, secondary- and tertiary-butyl, normal-amyl, isoamyl, secondary- and tertiary-amyl.

9. A method of inhibiting lipolysis in a mammal by administering to said mammal an effective amount of a composition of claim 8.

10. A method of treating ischemic heart disease and hypertriglyceridemia in a mammal by administering to said mammal an effective amount of a composition of claim 5.

11. 6-Quinolyl-4-methoxy carbanilate.
12. 5-Quinolyl-2-methoxy carbanilate.
13. 7-Quinolyl-3-methoxy carbanilate.
14. 7-Quinolyl-2-methyl carbanilate.
15. 7-Quinolyl-4-carbethoxy carbanilate.

* * * * *